United States Patent
Parkington (10) Patent No.: US 8,328,081 B2
(45) Date of Patent: Dec. 11, 2012

(54) METHOD AND SYSTEM FOR TRACKING SODIUM INTAKE

(76) Inventor: Sandra Parkington, San Diego, CA (US)

( * ) Notice: Subject to any disclaimer, the term of this patent is extended or adjusted under 35 U.S.C. 154(b) by 1066 days.

(21) Appl. No.: 10/756,179

(22) Filed: Jan. 12, 2004

(65) Prior Publication Data

US 2005/0150941 A1   Jul. 14, 2005

Related U.S. Application Data (60) Provisional application No. 60/441,058, filed on Jan. 16, 2003.

(51) Int. Cl.
*G06F 1/00* (2006.01)
(52) U.S. Cl. .......... 235/61 R; 600/300; 128/921
(58) Field of Classification Search .......... 600/300, 600/301; 128/921, 903–905, 920; 434/127
See application file for complete search history.

(56) References Cited

U.S. PATENT DOCUMENTS

| | | | |
|---|---|---|---|
| 2,150,442 A | 3/1939 | Herzog | |
| 2,956,358 A | 10/1960 | Pennington | |
| 3,572,584 A | 3/1971 | Weaver | |
| 4,048,477 A | 9/1977 | Hungerford | |
| 4,151,668 A | 5/1979 | Hungerford | |
| 4,951,197 A | 8/1990 | Mellinger | |
| 5,382,165 A | 1/1995 | Knox | |
| 5,412,560 A | 5/1995 | Dennison | |
| 5,640,774 A | 6/1997 | Goldman | |
| 5,704,350 A | 1/1998 | Williams | |
| 5,791,905 A | 8/1998 | Larson | |
| D401,613 S | 11/1998 | Goldman | |
| 5,915,854 A | 6/1999 | Burke | |
| 6,436,036 B1* | 8/2002 | Miller-Kovach et al. | 600/300 |
| 6,543,682 B1 | 4/2003 | Glaser | |
| 6,561,415 B2 | 5/2003 | Grant | |
| 2002/0133378 A1* | 9/2002 | Mault et al. | 705/3 |
| 2004/0162702 A1* | 8/2004 | Pandipati et al. | 702/173 |
| 2006/0064030 A1* | 3/2006 | Cosentino et al. | 600/547 |

* cited by examiner

*Primary Examiner* — Sam Yao
*Assistant Examiner* — Marie Archer
(74) *Attorney, Agent, or Firm* — Fredrikson & Byron, P.A.

(57) ABSTRACT

A calculating tabulating system which enables a person on a sodium restricted diet to better regulate the ingestion of sodium for prevention of medical complications. The system includes conversion of the weight of dietary sodium from a standard system of weights and measures to a simple numerical scale, conversion of the weight of dietary sodium consumed to the simple numerical scale, maintaining a running total of dietary sodium consumed in the simple numerical scale. The system includes various devices to aid in the conversion and tabulation process including various mechanical device and electronic devices.

9 Claims, 10 Drawing Sheets

SALTRAX™ ELECTRONIC CALCULATOR

| Intake Points (Sodium Points) | Weight of Dietary Sodium by Milligram (mg) |
|---|---|
| 0 | 0 to 49 mgs |
| 1 | 50 to 149 mgs |
| 2 | 150 to 249 mgs |
| 3 | 250 to 349 mgs |
| 4 | 350 to 449 mgs |
| 5 | 450 to 549 mgs |
| 6 | 550 to 649 mgs |
| 7 | 650 to 749 mgs |
| 8 | 750 to 849 mgs |
| 9 | 850 to 949 mgs |
| 10 | 950 to 1049 mgs |
| 11 | 1050 to 1149 mgs |

METHOD AND SYSTEM FOR TRACKING SODIUM INTAKE

The present application claims priority under 35 USC 119 (e) from U.S. provisional application Ser. No. 60/441,058 filed Jan. 16, 2003 and entitled Sodium Calculator Teaching Tool.

FIELD OF THE INVENTION

The present invention relates generally to methods and systems for tracking dietary intake. More particularly, the present invention relates to a method and a system for tracking daily dietary sodium intake.

BACKGROUND OF THE INVENTION

People diagnosed with heart failure (HF), high blood pressure (hypertension), renal failure or any disease where fluid balance is more critical compared to a healthy person, often have a difficult time understanding the relationship between dietary sodium intake and excessive fluid stressing the organ systems (e.g., pulmonary congestion/peripheral edema). As an example, a main reason for re-hospitalization for patients with HF is the dietary over indulgence of sodium. In the United States, as the population of people over 50 years of age grows, heart failure has become an increasingly common diagnosis. Over half of the hospital admissions for heart failure are because of fluid overload directly related to an excess of sodium in the diet.

Excess sodium intake shifts extra fluid into the bloodstream. The extra fluid makes it difficult for an already weakened heart to function properly and pump blood out to the rest of the body. This extra fluid has a tendency to back up into organs and extremities creating a condition known as edema. Edema can become life threatening when the person's lungs are not able to get enough oxygen due to an added fluid barrier during physiologic oxygen transfer. The excess fluid causes the patient to actually drown, also known as acute pulmonary edema.

In the spring of 2003, the National High Blood Pressure Education Program (NHBPEP), which is coordinated by National Heart, Lung, and Blood Institute (NHLBI), released updated hypertension guidelines. High blood pressure affects nearly 50 million people in the United States. Uncontrolled high blood pressure leads to a greater risk of heart attacks, heart failure, strokes and kidney disease. According to the recommendations, a lowered sodium intake to about 1600 mg. per day has the same effect as treatment with a single blood pressure lowering medication.

Physicians and nurses spend a significant amount of time teaching patients about the dangers of too much sodium in their diets. Often patients are only told, "take the salt shaker off of the table." Processed food is notoriously high in sodium, such as quick service products, canned soups, canned vegetables or frozen dinners. Telling patients with salt restrictions to avoid high sodium foods alone does not offer a specific method for answering the patient's main question of how to actually put this prescribed diet into daily practice.

In addition, the current method of measuring sodium in foods and beverages is often confusing to patients not accustomed to the metric system. Some labels use grams (Gms.) of sodium while others mention milligrams (mg.) of sodium. Whether the patient has a newly diagnosed problem requiring strict sodium balance or someone who has been dealing with the problem for years, the matter of regulating the salt intake is often a complicated and confusing aspect of self-care.

Thus what is needed is a system and method that allows the typical patient on restricted sodium to diet to track and record their daily dietary sodium intake. Such a system and method must be economical to implement, easy to understand, and simple to use.

SUMMARY OF THE INVENTION

It is an objective of the present invention to provide a system and method that allows the typical scientifically unsophisticated person to track daily sodium intake. It is also an objective of the present invention to provide a system and method that is economical, easy to implement and use. It is an additional object of the present invention to provide a range of economical and easy to use devices to assist an individual to track dietary sodium intake.

Using the Sodium Calculator Teaching Tool, patients following sodium-restricted diets would have an easy, uniform way to calculate sodium intake in their diets without having to learn complicated mathematical calculations. The method of using a system of one to two digit points to represent the hundreds and thousands of milligrams of sodium may lead to better compliance with the sodium restriction and thus fewer episodes of fluid overload necessitating costly physician visits, emergency room visits, and hospitalizations.

This new tool allows for less ambiguity and confusion when physicians, nurses, and nutritionists teach the important concept of sodium restriction to patients. Patients will be empowered to make appropriate food choices based on a system of uniform "points" rather than the often-confusing measurements: milligrams (mg.) or grams (Gms.) or the often repeated medical prescription to, "just take the salt shaker off the table".

The Sodium-Calculator Teaching Tool could be taught easily through nutrition education classes sponsored by a health insurance plan or hospital system. It also could be sold as a package of instructions, calculating tools, resource lists, etc. to the general public. There are not many general sources available for lay people that address this important nutritional issue. A recent search on Amazon.com for books that address salt and sodium restricted diets led to only three books, and each one addresses this topic in a non-specific manner. This method could eventually be used in the FDA Nutrition Food Labeling along with the listed grams and milligrams of sodium. This would allow for ease and less confusion when patients shop for low sodium foods. Restaurants and food corporations could use this system to label their sodium content in recipes and on their food wrappers and cups in an easily understood way.

There are many potential uses for this method. This new system offers a way to help the increasing numbers of persons following sodium restricted diets to cope with the challenging and confusing sources of salt intake that they must control. This improved sodium intake management offers a way to decrease expensive hospital admissions and re-admissions for fluid overload.

DESCRIPTION OF THE DRAWINGS

The invention will be better understood by an examination of the following description, together with the accompanying drawings, in which:

FIG. 7a is another alternative tool to calculate dietary sodium intake;

FIG. 7b is view of the card portion of the tool to calculate dietary sodium intake of FIG. 7a;

FIG. 7c is a perspective view of the slide of the tool depicted in FIG. 7a;

FIG. 7d is a side view of the slide to tool depicted in FIG. 7a;

DETAILED DESCRIPTION

The following detailed description should be read with reference to the drawings, in which like elements in different drawings are numbered identically. The drawings, which are not necessarily to scale, depict selected embodiments and are not intended to limit the scope of the invention. Examples of constructions, materials, dimensions, and manufacturing processes are provided for selected elements. All other elements employ that which is known to those of skill in the field of the invention. Those skilled in the art will recognize that many of the examples provided have suitable alternatives that can be utilized.

Figure 1:
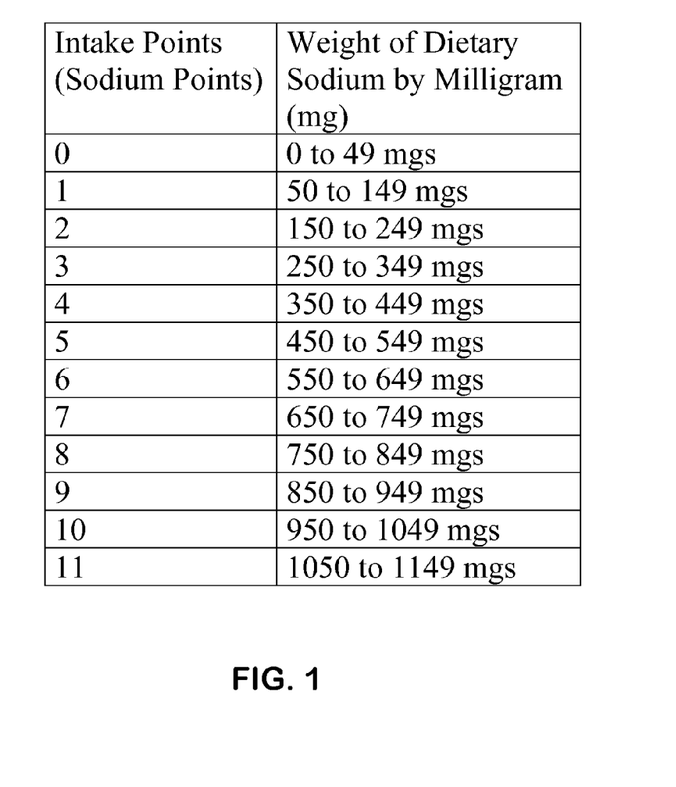
FIG. 1 is a table showing a preferred version of the relation between a weight scale and a number point scale with which the present invention is practiced.

One of the important aspects of the present invention is the creation of number or point scale wherein each number of the scale represents a set amount of dietary sodium (i.e. salt, NaCl, etc.). The relationship of the weight of dietary sodium to the numbers of the scale is based on a preset ratio. In a preferred embodiment of the present invention as discussed below, the ratio of dietary sodium by milligram to the points, intake points herein, is 100 mg to 1 intake point. However, the ratio could be 50 mg of dietary sodium to 1 intake point or 200 mg of dietary sodium to 1 intake point. FIG. 1 provides a table showing an easily read scale that relates intake or sodium points to milligrams of sodium.

Thus, under the preferred embodiment of the present invention, one sodium "point" or intake point represents a predetermined amount of dietary sodium. In the preferred embodiment, one "point" is approximately 100 milligrams (mg.) of sodium within the range of about 50 mg to about 150 mg, (FIG. 1). For example, a serving of a particular cereal contains 300 mg. of sodium. This amount of sodium would total "3 Points" under the present invention system. When sodium listed is not an even hundred, the patient would be taught to round down to the nearest whole point for any number less than half a point (i.e. less than 50 mg) and round up to the nearest whole point for any number over half a point (i.e. 50 mg or more).

Figure 2:
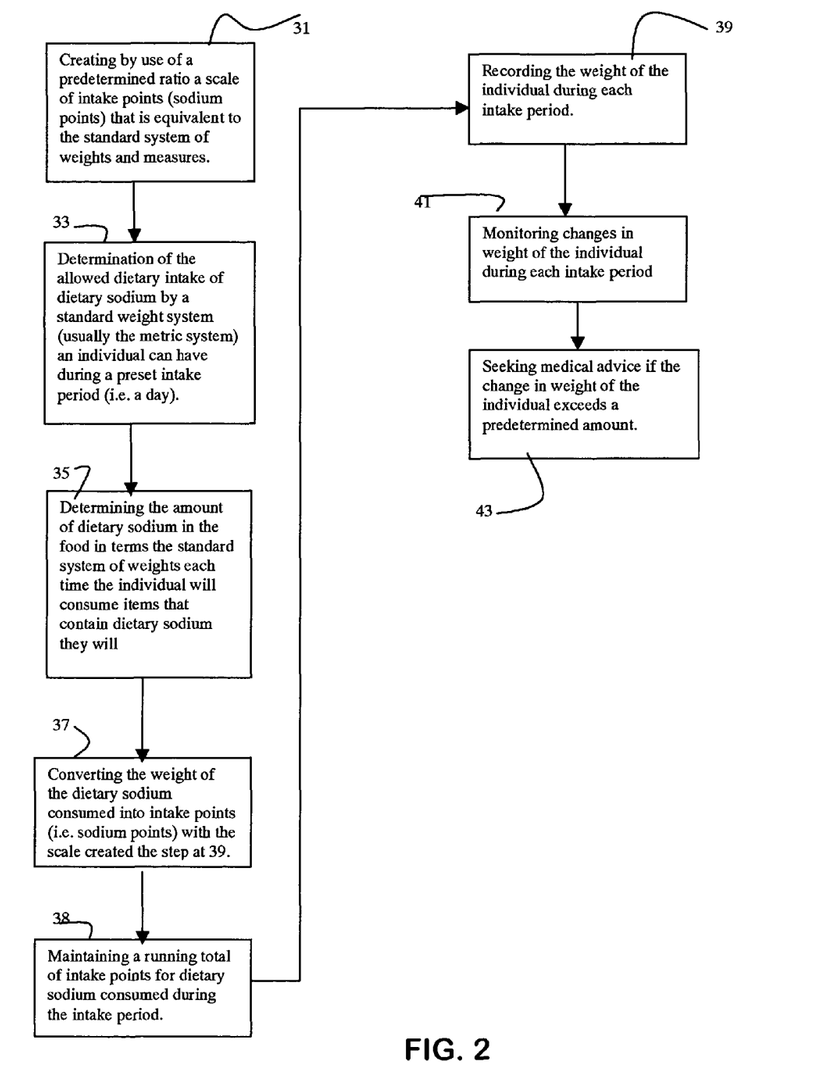
FIG. 2 is a flow chart of the overall system of the present invention.

The present invention, utilizing the scale discussed above, also provides a system for the tracking of dietary sodium ingestion that is quick, easy and effective for an individual to use. FIG. 2 is flow chart that depicts the fundamental steps of the system when used. After the establishment of the intake point or sodium point scale 31 the next step is the determination of the amount of dietary sodium that the patient or individual required to live on a sodium restricted diet 33. As noted above and again below the scale based in the preferred embodiment makes it easier to understand and track sodium intake. During an intake period, typically a day, the individual using the system will determine the amount of dietary sodium in various food items they consume 35. They will then convert the weight of the dietary sodium into intake points with the aid of the pre-established scale (FIG. 1) 37. The individual using the system will then maintain a running total of intake points equivalent to their dietary sodium consumption 38. The system includes several devices to aid in making the conversion to intake points and maintaining a running total that will be discussed in detail below.

In an additional aspect of the system the individual tracking dietary sodium intake will also record their body weight once per day, preferably in the morning 39. They will then monitor changes in their weight on a daily basis 41 and if it changes by more than a preset amount they may seek medical advice as needed 43. As noted elsewhere herein an individual on a restricted sodium diet is often on that diet because of certain physical conditions. A short-term change in weight can signal a significant worsening of the condition requiring prompt medical attention. Often the rapid weight losses or gains are related to body fluid status. In some cases a change of as little as two pounds is significant.

Patients following the dietary sodium calculating system of the present invention will be taught to track their daily sodium intake by tabulating points. Their daily point total should correlate with their daily sodium restriction, as prescribed by a physician. The system provides several different calculator tools, discussed below, to help patients track their daily sodium intake.

Figure 3:
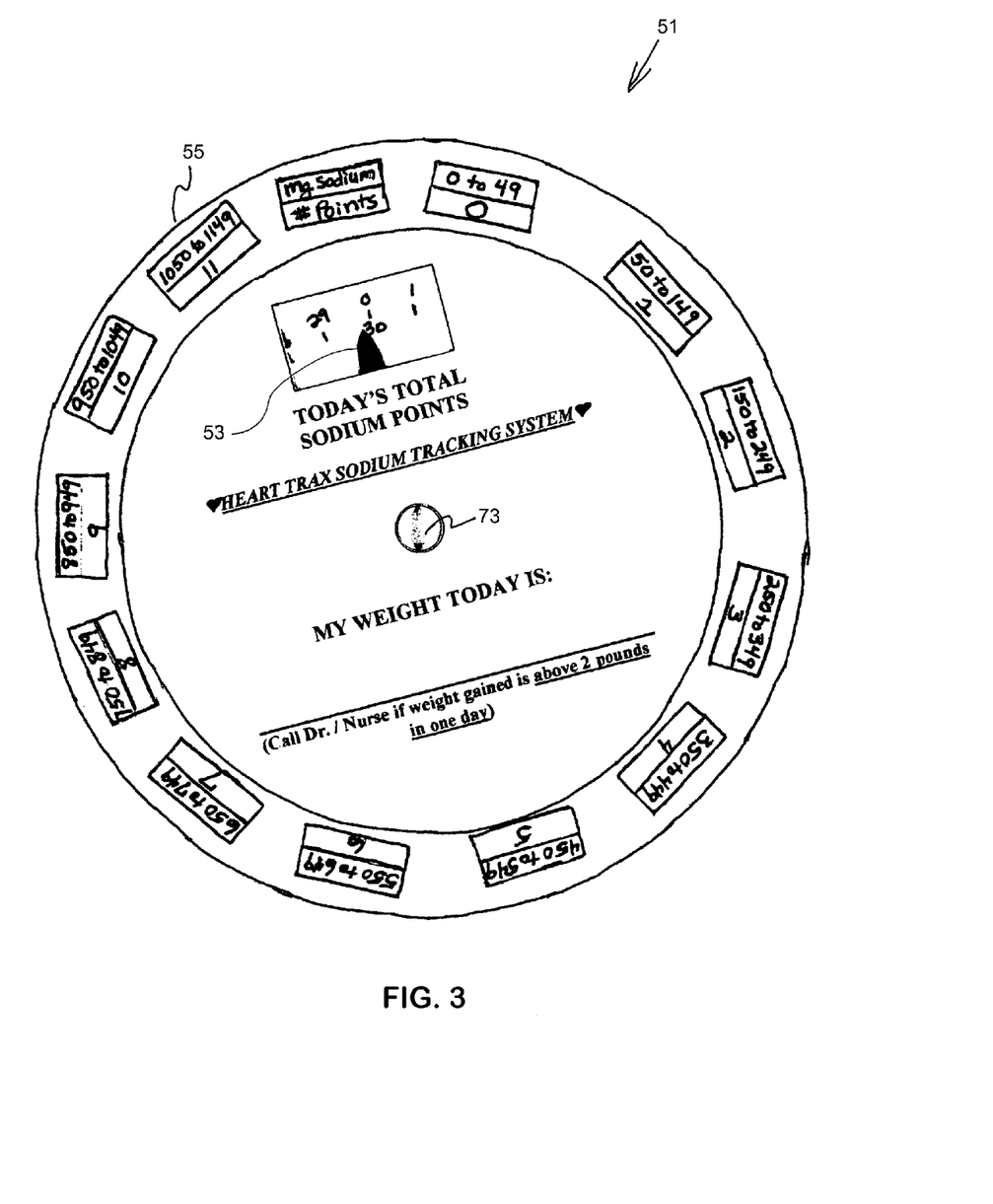
FIG. 3 is a preferred embodiment of the sodium calculation wheel of the present invention.

One preferred embodiment of a device 51 for tracking points is shown in FIG. 3 portrays a needle pointer 53 on a dial wheel 55 that may be rotated manually. The patient would total up the sodium points per meal and dial it in on the adding wheel or the patient may choose to keep track of daily sodium intake using the calculating beads or some other device discussed below. A typical HF patient may be placed on a restricted diet of 2 to 3 Grams of sodium per day. Most sodium found in pre-packaged foods is labeled using milligrams or "mg." Those working in the medical field may understand that 1000 mg. is the same as 1 Gram (Gm.) of sodium, however these two units of measure can be very confusing to the layperson.

Using this new system, a patient might be placed on the 20-point plan (2 Gm), 25-point plan (2.5 Gm), or the 30-point plan (3 Gm) sodium restriction. The patient needs to learn that the points must be spread evenly over 3-5 small meals/snacks throughout the day, rather than saved up to use at one meal. If a patient tries to save up sodium points and ingests them at one setting, the increased sodium intake might overwhelm the body and lead to serious fluid overload.

One method of distributing the sodium points is to teach a patient to keep a point value per meal in mind. For the 30-point plan, the patient would be limited to six points per meat or snack (assuming three meals, two snacks). The range for maximum flexibility at one meal could vary only by one to two points (per the advice of the healthcare provider) under or over the six allowed per meat (four to eight points) as long as the daily total is not exceeded.

As an example of using the sodium points system: A person on the 30-point plan chooses to eat—6 points of sodium at breakfast—6 points for lunch—6 points for dinner for a total of 18 meal points, leaving 12 points for snacks, divided in no more than 6 points per sitting.

The sodium calculator tool would teach patients how to add up the points to reach a daily total. A resource, listing commonly eaten foods, their amounts and their sodium "point" value would also be made available. In addition, patients would be taught how to easily make the conversion themselves using the calculator tool. The calculator tool will be able to keep a running daily total for the patient to keep track of their sodium intake during the day. With continued use of this tool, it is hoped that the patient would be able to calculate sodium content easily and quickly, thus potentially preventing the fluid overload and its complications.

Patients would also be taught the importance of weighing themselves daily and keeping track of this number. Increased sodium intake leads to rapid gains in weight as the body retains fluid. Daily weights are the way that patients will be able to tell whether the correct sodium restriction level is being followed. A place to enter that daily weight will be in the tool as well with specific instructions for when it is appropriate to contact the health care provider.

Figure 4:
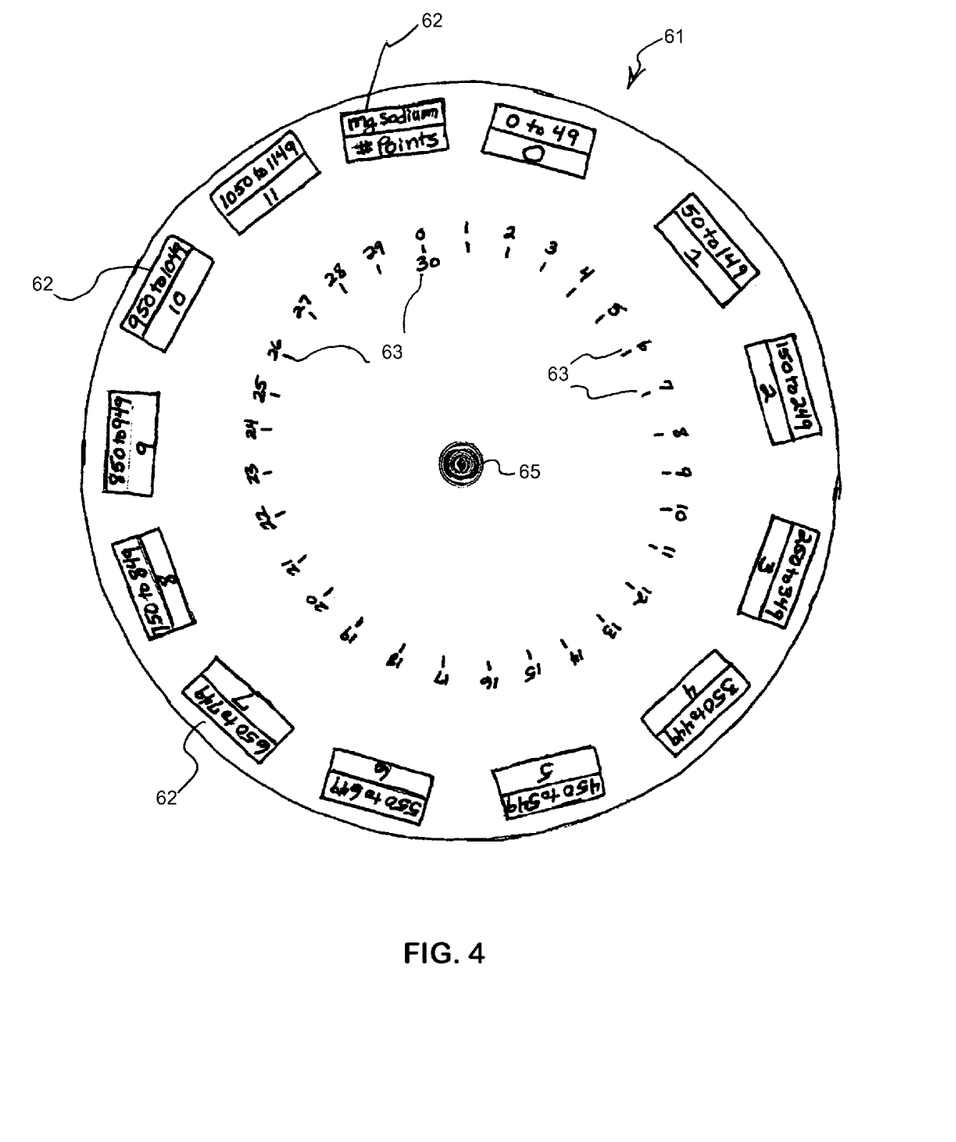
FIG. 4 is the first part of a sodium intake calculation wheel of the present invention.
Figure 5:
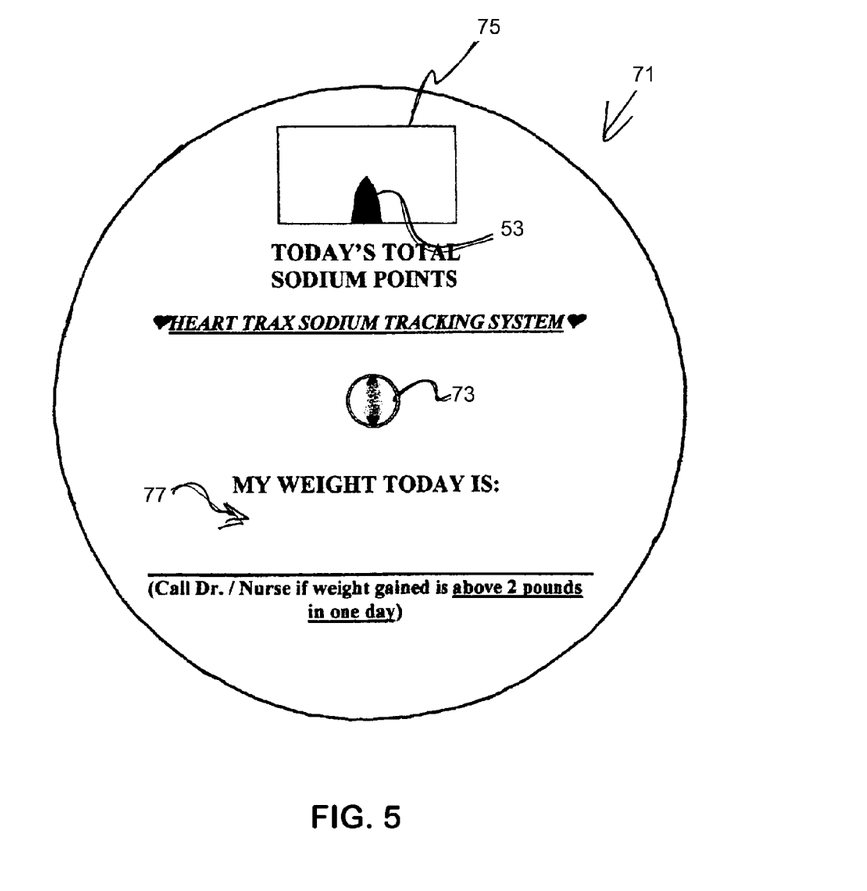
FIG. 5 is the second part of a sodium intake calculation wheel.

The calculation wheel 51 depicted in FIG. 3 has two parts, a bottom sheet or disk 61, FIG. 4 and a top sheet or disk 71 FIG. 5. The bottom disk 61 FIG. 4 of the calculation wheel has an outer ring of numbers 62 that illustrates the conversion of milligrams of sodium to points. Disk 61 also has inner ring of numbers 63 that allow for the daily accumulation of points after each time the individual using the calculation wheel ingests sodium. The inner ring of numbers 63 are used in conjunction with the top sheet or disk 71 of the calculation wheel 51. Top disk 71 is rotationally attached at center 73 to the center 65 of bottom disk 61.

The top disk 71 of the calculation wheel has a window 75 with to view the accumulation of sodium points 63 as the top disk 71 is rotated about center 73 on top of bottom disk 61. Top disk 71 includes a space 77 to record daily weight for comparison against desired weight. The surface of this portion of the calculation wheel is made from materials to allow the daily weight to be wiped off.

As previously noted FIG. 3, shows both parts 61 and 71 of the calculation wheel 51 rotateably attached at their respective centers 73 and 65. Top disk 71 can be rotated in either a clockwise or counter clockwise direction. However, given the orientation of scale 63, to tabulate or sum total intake points or sodium points top disk would be progressively rotated in a clockwise direction around the point of attachment 73 to maintain a running total.

Figure 6:
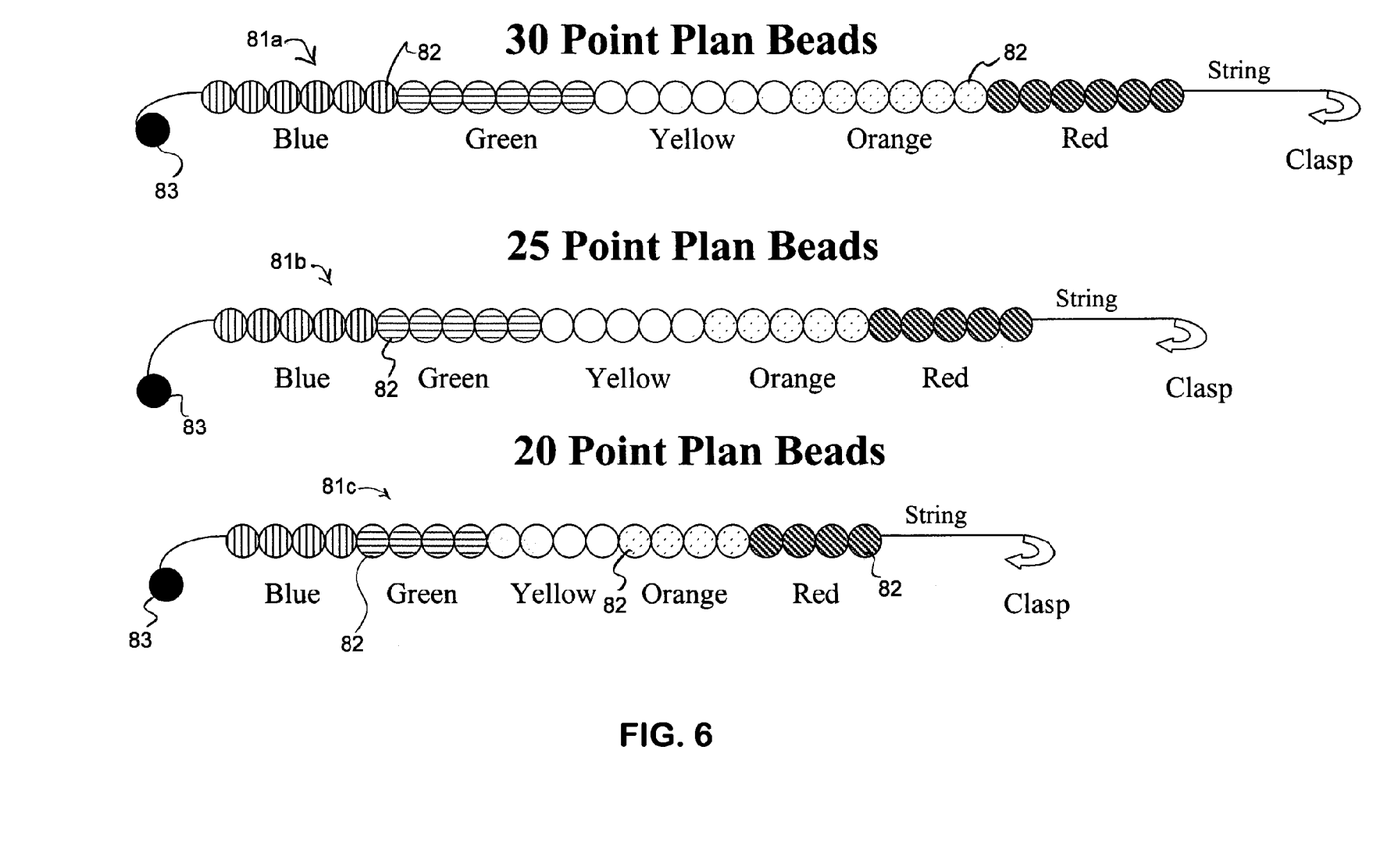
FIG. 6 is an alternative tool to calculate dietary sodium intake.

FIG. 6 depicts three variations of an alternate mechanical embodiment, 81a, 81b and 81c, of the calculating tool for tracking sodium ingestion based on points. Points are represented by different colored beads 82. A marking device is advanced by the user for the number of points of sodium ingested. FIG. 6 depicts three different bead rings 81a, 81b, and 81c. In the preferred embodiments depicted each bead represents one sodium point or 100 mg. of sodium. Each Bead 82 Counts as ONE sodium point (100 mg. of sodium). The health care provider will prescribe a daily-allowed intake of sodium per patient. The health care provider will prescribe the beaded string that corresponds to the patient's prescription: 30 Point 81a, 25 Point 81b, or 20 Point 81c Plan.

The colored beads in each strand correspond with the number of Points allowed for each meat or snack (Total of 3 meats+2 snacks). The patient must not eat food that has a sodium amount equivalent to any more than the allowed number of beads (sodium points) per meat or snack: 6 Beads per meal/snack for the 30 Point plan, 5 Beads per meal/snack for the 25 Point plan and 4 Beads per meal/snack for the 20 Point plan. He/she will be instructed to discuss any changes in advance with the health care provider. The patient wilt be instructed not to save up all the beads (sodium points) for any one meal or snack in order to eat them at another daily meat or snack (this may overload the body with sodium and lead to fluid retention problems).

After each meal/snack, the patient moves the closeable clasp 83 (right side of diagram) forward along the left side to the right side of the beaded string according to how many points of sodium were eaten. This beaded string may be carried in a purse, a pocket, or worn on the wrist for ease of use. The patient will progress each calendar day from the dark colored Blue beads (left in the diagram) to the Red colored beads. The Red color will remind the patient that he/she is reaching his/her daily limit of sodium points.

Figures 7A, 7B, 7C, 7D:
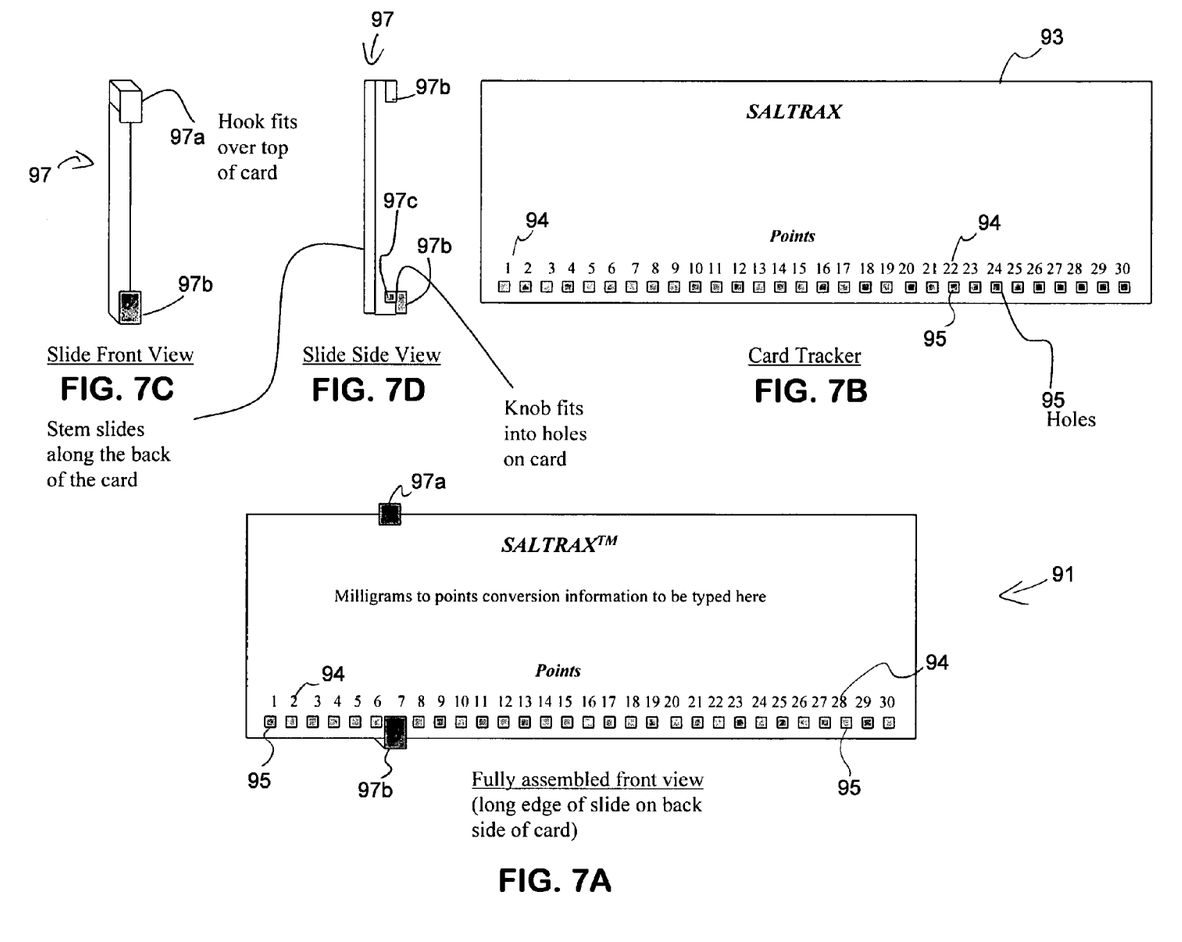

FIG. 7 is another alternate mechanical embodiment 91 of the calculator of the present invention. Calculator 91 in FIG. 7 is a linear version of the calculator or tabulator. The calculator 91 (FIG. 7a) consists of a card 93 (FIG. 7b) with a sequential series of numbered 94 holes 95 at the bottom set out in a linear array. A slide 94 (FIG. 7c) attaches to the card 93 at it backside, not shown. As depicted in FIG. 7a hook 97a of slide 97 fits one the top of card 93 and knob 97b fits over the bottom of card 93. The user of the card can move slide 97 along card 93 and flange 97c of knob 97b will click into each hole to detachably but securely hold the slide in place. Thus, the user can keep track of sodium intake.

Figure 8:
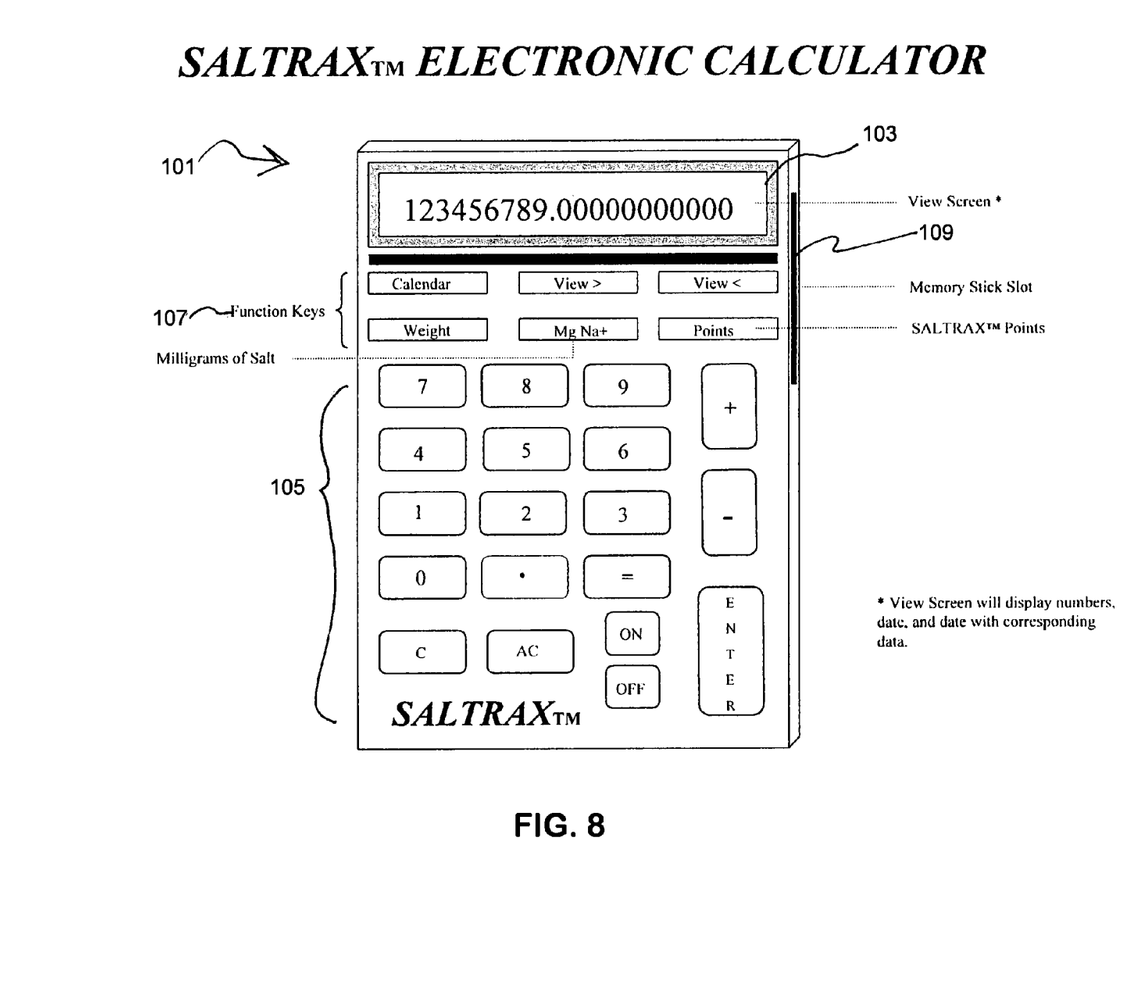
FIG. 8 is an electronic device for calculation of intake of dietary sodium.

FIG. 8 is an embodiment of the present invention in an electronic calculator format 101. In a preferred embodiment calculator 101 would be a programmable calculator that would include a display 103, keypad 105, special function keys 107 and a memory slot for a memory stick ("memory stick" is a known industry term for a device which contains a memory chip to which data is downloaded) or some other similar device. Calculator 101 would also include cpu, internal memory and other circuitry typical for such electronic devices and so well known in the art that it is not necessary to discuss them at all in detail. The conversion scale depicted in FIG. 1 can be programmed into the memory of the calculator and displayed when needed. However, the calculator has the added advantage of simply allowing an individual using the system to enter the weight of the dietary sodium that will be ingested and running a calculation to obtain the corresponding intake of sodium point or points. The user would push key 107a (calendar) and use keys 107b & 107c (View<>) to arrive and the desired date. Then the user pushes key 107d (Weight) to enter his/her body weight for the intake period (usually taken at the beginning of the day). After each meal or snack the user pushes key 107e (Mg Na+) and enters the amount of milligrams of sodium ingested. The system will automatically run a routine that would perform the conversion of milligrams to the point system. If the user wishes to enter points directly he/she may bypass key 107e and press key 107f to enter points of sodium consumed.

These same function keys, 107a-f, are used to view the stored data by calendar date. Thus, one could maintain a record of sodium intake over an extended period of time. The information on sodium intake, including amount and time, could then be made available to the individual's caregiver either directly or via removable memory stick, which could be used to download the data into the caregiver's database. This would provide important information for treatment, research or otherwise. Additionally, by maintaining a record as to time of entry during the day an evaluation could be made of a person's intake each time they eat.

Once the description of the invention is read and understood by those skilled in the art it will understand how the system of the present invention can be implemented on a wide variety of programmable computer systems ranging from home computers to personal digital assistants (PDA's), etc. This would allow for distribution of the system in a software format useable on a wide variety of electronic formats. FIG. 1 showing the overall functional components of the system could serve as a basis for a general software program with various subroutines to fully implement the present invention. Additionally, the functions of the mechanical calculator or electronic calculator would naturally be implemented as part of the software package.

Figure 9:
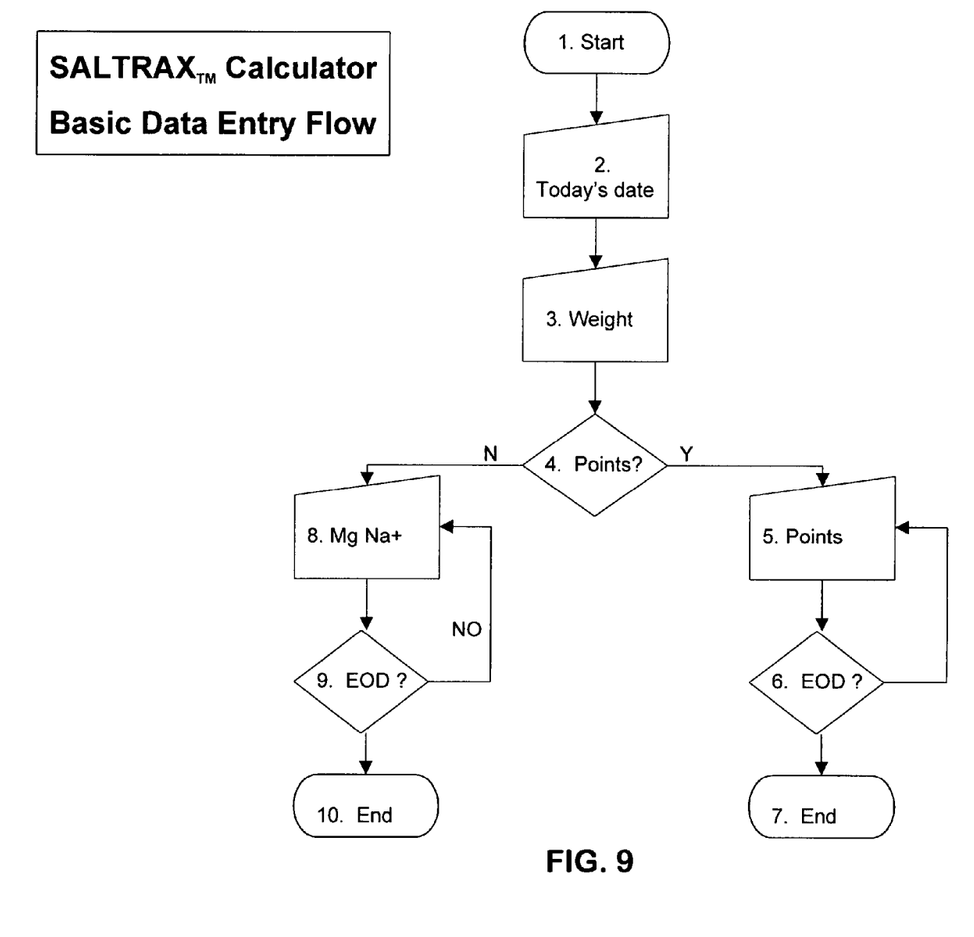
FIG. 9 is a flow chart of one variation of a data entry routine for an electronic calculator similar to that depicted in FIG. 8.

FIG. 9, a flow chart, is an example of a basic data entry routine that could be implemented in software on the calculator depicted in FIG. 8 or any typical programmable computer. The system will thus track and store the intake of sodium per meal per day. The data may be entered by milligrams of sodium or points (if the user feels comfortable with using the point system). The calculator will perform the conversion of milligrams to points in the data view mode described later. In order that the data be more portable for use by the medical service provider a "Memory Stick" or similar data storage device will be inserted into the calculator whereupon pressing the on button data will be transferred for storage.

The data entry routine set forth in FIG. 9 is as follows: 1) Start: Turn on the calculator by pressing the on button. 2) Today'sDate: Press the calendar button. When calendar appears press the view buttons in either direction (up or down) to arrive at today's date and press enter. 3) Weight: Press the weight button and enter your weight in pounds as of the morning of the selected date and press enter. 4) Points?: Decision . . . the calculator gives you the option of tracking salt by points or milligrams. 5) Points: If you choose to enter data by points press the point button and enter the points of sodium intake and press the plus button and enter button. This is to be done after each meal. The calculator wilt retain the points entered and add each additional entry to the preceding total for that day. 6) EOD?: Decision . . . if you have not reached the End Of Day (i.e., the last meal of the day for which you are entering data), repeat step 5. If you have, proceed to step 7. 7) End: Upon making the final entry of the day press the off button. The calculator will store the final tally of points for the date selected. 8) MgNa+: If you choose to enter data in milligrams of sodium (Mg Na+) press the Mg button and enter the milligrams of sodium intake and press the plus button and enter button. This is to be done after each meal. The calculator will retain the milligrams entered and add each additional entry to the preceding total for that day. 9) EOD?: Decision . . . if you have not reached the End Of Day (i.e., the last meal of the day for which you are entering data, repeat step 8. If you have, proceed to step 10. 10) End: Upon making the final entry of the day press the off button. The calculator will store the final tally of points for the date selected.

The system will store data entered by date, milligrams, and points. These data may be viewed by the user on the calculator itself or by extracting the "Memory Stick" and downloading the data contained to another computing device such as, laptops, hand held computers, and desktop computers. The information may be made available to the healthcare provider electronically in the same download manner.

Figure 10:
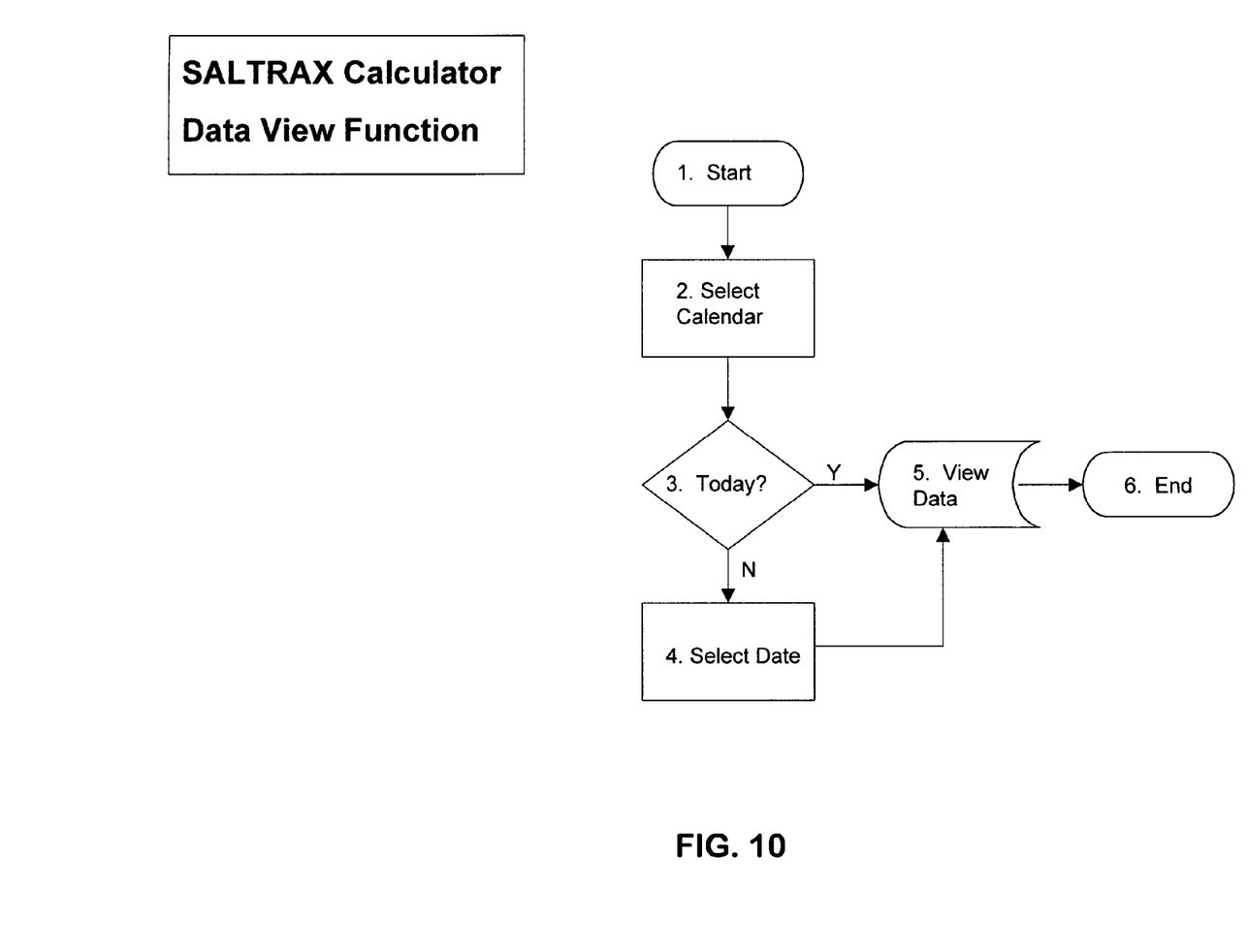
FIG. 10 is a flow chart of one variation of data view routine on an electronic calculator similar to that depicted in FIG. 8.

The data view routine depicted in FIG. 10 is as follows: 1) Start: Turn on the calculator by pressing the on button. If the data you wish to view is stored on a Memory Stick, insert the card into the calculator before turning it on. 2) SelectCalendar: Press the calendar button to activate the calendar mode. 3) Today: If the current displayed calendar date is the date for which you wish to view data go to step 5. If not, proceed to step 5. 4) SelectDate: Select the date for which you wish to view data by scrolling up or down using the view buttons. 5) ViewData: Once the calendar is displaying the correct date simply view the data for that date on the screen. 6) End: Turn off the calculator. The Memory Stick may be removed and stored separately.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention.

I claim:

1. A method for tracking sodium intake comprising the steps of:
   a. determining an amount by weight, of a standard measurement system, of dietary sodium a subject is allowed to consume during an intake period, the amount being specific to a particular subject;
   b. converting the amount by weight of dietary sodium so determined into intake points by use of a preset ratio of only the amount by weight of the standard measurement system to intake points, the conversion being performed by a processor and the preset ratio being programmable into the processor, the preset ratio resulting in a total number of the intake points the subject is allowed to consume during an intake period that is one or two digits long;
   c. selectively displaying on a display a conversion scale listing the relationship between multiple intake point values and the corresponding amounts by weight of dietary sodium, the multiple relationships being displayed simultaneously and being based on the preset ratio, the display operatively connected to the processor;
   d. determining the amount by weight of the standard measurement system of dietary sodium in a portion of food that will be consumed by the subject;
   e. selectively entering into the processor the number of intake points associated with the portion of food that will be consumed or the amount by weight of the standard measurement system of dietary sodium in a portion of food that will be consumed, such entry into the processor of the number of intake points or the amount by weight of dietary sodium being user-selectable;
   f. converting the amount by weight of the standard measurement system of dietary sodium in the portion of food to be consumed to intake points by use of said preset ratio;
   g. maintaining a running sum of intake points which are equivalent to dietary sodium consumed by the subject during the intake period; and
   h. displaying as an output the running sum of intake points on the display.

2. The method of claim 1 including the further step of repeating steps a. to h. for successive intake periods.

3. The method of claim 2 including the further step of making each intake period a day.

4. The method of claim 1 including the further steps of:
   i. recording the weight of the subject at the beginning of reach intake period; and
   j. recording the weight of the subject at least once per day.

5. The method of claim 4 including the further steps of:
   k. determining the change in weight between the weight recorded at the beginning of the intake period as compared to the weight taken at the beginning of the previous intake period;
   l. determining if the change in weight exceeds a preset threshold amount; and;

m. taking remedial action if the change of weight exceeds the threshold amount.

6. The method of claim 5 wherein the step of taking remedial action is consulting with a health specialist.

7. The method of claim 1 wherein the standard measurement system used is selected from the group of the English system or the Metric system.

8. The method of claim 1 wherein the standard measurement system is the Metric system.

9. The method of claim 8 wherein the preset ratio is 100 milligrams of sodium per 1 intake point.

* * * * *